United States Patent
Suzuki et al.

(10) Patent No.: US 11,224,667 B2
(45) Date of Patent: Jan. 18, 2022

(54) 11C-LABELED CATECHOL DERIVATIVE, PET PROBE OF PHOSPHORYLATED TAU AGGREGATION INHIBITOR USING THE SAME, AND PRODUCTION METHOD OF THE SAME

(71) Applicant: NATIONAL CENTER FOR GERIATRICS AND GERONTOLOGY, Obu (JP)

(72) Inventors: Masaaki Suzuki, Obu (JP); Kengo Ito, Obu (JP); Takashi Kato, Obu (JP); Hiroshi Ikenuma, Obu (JP); Hiroko Koyama, Obu (JP)

(73) Assignee: NATIONAL CENTER FOR GERIATRICS AND GERONTOLOGY, Obu (JP)

( * ) Notice: Subject to any disclaimer, the term of this patent is extended or adjusted under 35 U.S.C. 154(b) by 440 days.

(21) Appl. No.: 16/315,305

(22) PCT Filed: Jun. 30, 2017

(86) PCT No.: PCT/JP2017/024166
§ 371 (c)(1),
(2) Date: Jan. 4, 2019

(87) PCT Pub. No.: WO2018/008552
PCT Pub. Date: Jan. 11, 2018

(65) Prior Publication Data
US 2021/0205481 A1    Jul. 8, 2021

(51) Int. Cl.
*C07C 213/04* (2006.01)
*A61K 51/04* (2006.01)
*C07B 59/00* (2006.01)

(52) U.S. Cl.
CPC .......... *A61K 51/04* (2013.01); *C07B 59/001* (2013.01); *C07B 2200/05* (2013.01)

(58) Field of Classification Search
None
See application file for complete search history.

(56) References Cited

U.S. PATENT DOCUMENTS

2014/0249180 A1    9/2014 Takashima et al.

FOREIGN PATENT DOCUMENTS

| EP | 2 764 863 A1 | 8/2014 |
| WO | WO 2013/051266 A1 | 4/2013 |

OTHER PUBLICATIONS

Mach et al. (Development of 18F & 11C-Labeled Radiopharmaceuticals, 2008, vol. 14, Lesson 2, pp. 1-22) (Year: 2008).*

(Continued)

*Primary Examiner* — Sudhakar Katakam
*Assistant Examiner* — Jennifer C Sawyer
(74) *Attorney, Agent, or Firm* — Birch, Stewart, Kolasch & Birch, LLP

(57) ABSTRACT

An object of the invention is to provide an $^{11}$C-labeled catechol derivative having sufficient radioactivity to obtain an imaging image by a PET apparatus, a PET probe of a phosphorylated tau aggregation inhibitor using the same, and a method for producing them. The $^{11}$C-labeled catechol derivative of the present invention is represented by the following general formula (a) (wherein R is a substituent having an isopropylamino group, and the carbon at the 2-position of the isopropylamino group is labeled with $^{11}$C).

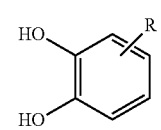

(a)

7 Claims, 2 Drawing Sheets

A1 second reaction vessel

A2 first reaction vessel

B1 second reaction vessel

B2 first reaction vessel

(56) References Cited

OTHER PUBLICATIONS

Leis et al. (Rapid Comm. Mass Spec., 1988, vol. 2, No. 12, pp. 263) (Year: 1988).*

Ikenuma et al., "Synthesis of (R,S)-isoproterenol, an inhibitor of tau aggregation, as an $^{11}$C-labeled PET tracer via reductive alkylation of (R,S)-norephinephrine with [2-$^{11}$C]acetone," Bioorganic & Medicinal Chemistry Letters (2019), vol. 29, pp. 2107-2111.

International Search Report, issued in PCT/JP2017/024166, dated Oct. 3, 2017.

Münch et al., "Evaluation of sympathetic nerve terminals with [$^{11}$C]epinephrine and [$^{11}$C]hydroxyephedrine and positron emission tomography"., Circulation. Feb. 8, 2000, vol. 101, No. 5, pp. 516-523, ISSN 1524-4539.

Soeda et al., "Toxic tau oligomer formation blocked by capping of cysteine residues with 1,2-dihydroxybenzene groups", Nat. Commun., Dec. 16, 2015, vol. 6, 10216, total 12 pages, ISSN 2041-1723.

Studenov et al., "High Yield Synthesis of [$^{11}$C],Acetone Through Selective Quenching of Methyl Lithium", Nuclear Medicine & Biology, 1999, vol. 26, pp. 431-435.

Van der Meij et al., "Reductive N-alkylation of secondary amines with [2-$^{11}$C]acetone", J.Label.Compd. Radiopharm., Oct. 15, 2003,vol. 46, No. 11,pp. 1075-1085, ISSN 1099-1344.

Written Opinion of the International Searching Authority, issued in PCT/JP2017/024166, dated Oct. 3, 2017.

Chinese Office Action and Search Report for Chinese Application No. 201780041574.5, dated Dec. 15, 2020, with an English translation.

Kong, "The Establishment of Neural Molecular Imaging Technology Platform—Experimental and Clinical Studies on Aβ and NFTs PET Imaging Based Dual-target Molecular Probes for Early Diagnosis of AD," 2016, 30 pages total.

Van Der Meij et al., "Reductive N-alkylation of secondary amines with [2-11 C]acetone," Journal of Labelled Compounds and Radiopharmaceuticals, vol. 46, 2003, pp. 1075-1085, 11 pages total.

* cited by examiner

11C-LABELED CATECHOL DERIVATIVE, PET PROBE OF PHOSPHORYLATED TAU AGGREGATION INHIBITOR USING THE SAME, AND PRODUCTION METHOD OF THE SAME

TECHNICAL FIELD

The present invention relates to a $^{11}$C-labeled catechol derivative, a PET probe of phosphorylated tau aggregation inhibitor using the same, and a production method of the same.

BACKGROUND ART

Alzheimer's disease (AD) is a type of dementia whose main symptom is cognitive decline and personality changes. Dementia is a common disease that affects about 25% of the Japanese population over the age of 85, AD accounts for about half of them. The number of AD patients is expected to increase steadily towards the anticipated aging society, and it is a serious problem in Japan where the declining birthrate and aging population advances.

Conventional AD studies predominantly based on the amyloid ß hypothesis that the abnormality of amyloid ß peptide is triggered by the onset of AD. Based on this hypothesis, when examining the brain of a person who was given anti-amyloid ß monoclonal antibody therapy, dementia progressed despite the disappearance of the amyloid ß peptide, it was not able to improve the effect which was expected for AD treatment.

For this reason, tau protein has recently attracted attention as a cause of AD onset other than abnormality of amyloid ß peptide. Tau protein is abundant in central nervous cells and is a protein indispensable for the function of the nerve axon which constitutes the neural network of the brain. In diseases such as Alzheimer's disease and familial frontotemporal dementia, it has become clear that cognitive symptoms appear due to hyperphosphorylation of tau of microtubule-associated protein, promoting the formation of neurofibrillary tangles. It has also been demonstrated that abnormality occurs in nerve cells only by aggregating and accumulating tau protein in the brain.

In addition, Takashima et al. Department of Aging Neurobiology in Center for Development of Advanced Medicine for Dementia, National Center for Geriatrics and Gerontology, screened compounds that suppress the aggregation of tau protein from natural compound libraries and drugs with catechol nuclei such as dopamine and adrenaline inhibited aggregation of tau protein (See Patent Document 1). Furthermore, when D/L-isoproterenol (a medicament used for exsanguination and bronchial asthma) among medicines having a catechol nucleus was administered to hyperphosphorylated tau-expressing mice, suppression of aggregation of tau protein and suppression of nerve cell dropout accompanying it resulted in a breakthrough effect of reduction of nerve activity and improvement of abnormal behavior (Patent Document 1).

PRIOR ART DOCUMENTS

Patent Documents

Patent Document 1: WO 2013-051266A

SUMMARY OF THE INVENTION

Problems to be Solved by the Invention

In order to investigate the mechanism of the inhibitory effect of the tau protein aggregation inhibitor having the catechol nucleus described above, it is important to investigate the in vivo dynamics of which part of the living body the inhibitor accumulates and how it moves. This study shows the location of the target protein, the metabolic stability of the drug, the excretion process, etc., as well as knowledge on toxicity development such as retention in specific organs. It is conceivable to prepare a tau protein agglutination inhibitor labeled with $^{11}$C as a method for analyzing the in vivo kinetics, and microdosing it directly to a mouse or a human to obtain an image with a PET apparatus. The PET apparatus is a device for administering a tracer labeled with a short-lived radionuclide releasing a positron such as $^{11}$C into a living body, measuring y rays generated by the tracer with a PET camera, and imaging the distribution in the body with a computer. By using the PET device, it is possible to track the drug behavior of the drug and reach to the target site noninvasively and quantitatively in living organisms including small animals and humans. Therefore, by analyzing the $^{11}$C PET image of the tau protein aggregation inhibitor having catechol nucleus, invasive imaging becomes possible and very useful information can be obtained in various fields such as biology, medicine development, medical care.

However, since half-life of $^{11}$C is as short as 20 minutes, it must be performed within 2 to 3 times the half-life from the completion of irradiation by the cyclotron to synthesis and purification. In addition, since the catecholamine skeleton is extremely easily oxidized and decomposed, it is extremely difficult to separate and purify from the reaction solution even if it can be synthesized in a short time. Due to such time constraints and chemical instability, there have been no examples of successful labeling of isoproterenol with catechol nucleus by $^{11}$C to date.

The present invention has been made in view of the above conventional problems, and it is an object of the present invention to provide an $^{11}$C-labeled catechol derivative having sufficient radioactivity for obtaining an imaging image by a PET apparatus, a PET probe of a phosphorylated tau aggregation inhibitor using the same, and a method of producing them.

Means for Solving the Problems

The $^{11}$C-labeled catechol derivative of the present invention is represented by the following general formula (a) (wherein R is a substituent having an isopropylamino group, and the carbon at the 2-position of the isopropylamino group is labeled with $^{11}$C).

[Formula 1]

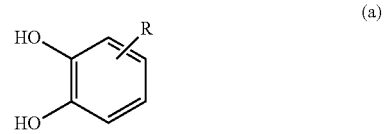

(a)

As described above, it has been found that various catechol derivatives such as dopamine and adrenaline inhibit aggregation of tau protein (Patent Document 1). From these facts, it is expected that the catechol derivative represented by the above general formula (a) can also inhibit the aggregation of tau protein, and since it is further labeled with $^{11}$C, it can be used for imaging by the PET method, it can be used for the in vivo dynamics study of inhibitors related to suppression of aggregation of tau protein.

Since unlabeled isoproterenol particularly strongly suppresses aggregation of tau protein and is expected as a drug for Alzheimer type dementia, among the catechol derivatives represented by the above general formula (a), $^{11}$C-labeled catechol derivative represented by the following structural formula (b) in which the carbon at the 2-position of the isopropylamino group of isoproterenol is labeled with $^{11}$C (In the formula, the carbon of * is marked with $^{11}$C), is extremely useful for studying the action of isoproterenol in vivo, the cause of Alzheimer's type dementia, and the like. The carbon to which a hydroxyl group is bonded in the structural formula (b) is an asymmetric carbon and the structural formula (b) is a compound in which an optical isomer exists. But the catechol derivative represented by the structural formula (b) of the present invention is a concept including an R form, an S form, a racemic form, a mixture of R and S forms at an arbitrary ratio. An $^{11}$C labeled product of a chiral compound of (R)-isoproterenol and (S)-isoproterenol can be synthesized using chiral noradrenaline as a raw material, or $^{11}$C-labeled substance is synthesized in racemic form and separated and purified by a chiral column.

[Formula 2]

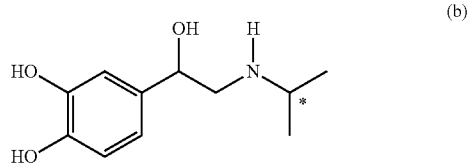

(b)

The $^{11}$C-labeled catechol derivative represented by the above general formula (a) can be prepared by subjecting a catechol derivative represented by the following general formula (c) (wherein R 1 represents a substituent having a primary or secondary amine) and [2-$^{11}$C] acetone to a reductive alkylation reaction in the presence of a reducing agent.

For example, [$^{11}$C] acetone can be prepared by capturing [$^{11}$C] CO$_2$ with an ether solution of excess methyllithium (CH$_3$Li). According to the conventional method, diphenylamine selectively decomposes excess methyllithium, the resulting lithium diphenylamine and dilithium [2-$^{11}$C]propane-2,2-bis(olate) ((CH$_3$)$_2$C(OLi)$_2$) intermediate are decomposed with strong acid (hydrogen chloride or sulfuric acid), but when this operation is carried out, iminium ions may be by-produced by reaction of the resulting diphenylamine with [2-$^{11}$C] acetone, and it is impossible to reproduce the desired [2-$^{11}$C] acetone reproducibly. But by treating with a weak acid, phenol (pKa value: 9.9) instead of a strong acid, such condensation reaction does not occur and [2-$^{11}$C] acetone can be obtained reproducibly.

In addition, since the reaction rate of the subsequent reductive alkylation reaction largely depends on the substrate concentration and the reaction solution, it is preferable to distill [2-$^{11}$C] acetone (boiling point 56° C.) prepared in the first reaction vessel and collect in a second reaction vessel to carry out a reductive alkylation reaction. When THF (boiling point 65° C.) or diethyl ether (boiling point 35° C.) having a low boiling point is used as a reaction solvent, the reaction efficiency decreases due to contamination of the ether solvent which suppresses the reductive alkylation reaction into the second reaction vessel by the azeotrope with [2-$^{11}$C] acetone. In this regard, the yield of the reductive alkylation reaction can be increased by using cyclopentyl methyl ether having a boiling point as high as 106°. In addition, cyclopentyl methyl ether is easier to dehydrate than common ether solvents such as dimethyl ether, so it is preferable as a solvent for [2-$^{11}$C]acetone synthesis, which is a water-blocking reaction.

[Formula 3]

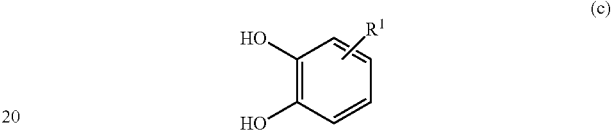

(c)

When the catechol derivative represented by the general formula (c) is norepinephrine (ie, noradrenaline), an $^{11}$C-labeled catechol derivative represented by the above structural formula (b), in which the carbon at the 2-position of the isopropylamino group of isoproterenol is labeled with $^{11}$C, can be produced.

As the reducing agent used in the reductive alkylation reaction, for example, sodium cyanoborohydride (NaBH$_3$CN), sodium triacetoxyborohydride (NaBH(OAc)$_3$) and the like can be used. Sodium triacetoxyborohydride (NaBH(OAc)$_3$) is preferred from the viewpoint of lower toxicity. In general, acetic acid having a pKa value of 4.76 is often used as the acid catalyst in the reductive alkylation reaction, but according to the test results of the present inventors, it was found that the reaction proceeds efficiently by using an acid having a pKa value of 3.7 or more and 4.8 or less. When the pKa value is less than 3.7 (eg, hydrochloric acid, the formation of the imine intermediate (iminium salt in the case of secondary amine) with [2-$^{11}$C]acetone and the primary amine is promoted, but the reducing agent (such as sodium triacetoxyborohydride) reducing the imine intermediate (iminium salt in the case of secondary amine) may be quickly decomposed. On the other hand, if the pKa value exceeds 4.8, the reduction reaction is slow, and autoxidation and decomposition of catechol nucleus by oxygen progresses during the reduction reaction. When synthesizing $^{11}$C-labeled isoproterenol, it is found out that high yield is obtained (radio-HPLC (Analytical yield: 79.5%) when NaBH$_3$CN is used as a reducing agent and acetic acid (pKa=4.76) is used as an acid, high yield is also obtained (radio HPLC analysis yield 87%) when using NaBH(OAc)$_3$ is used as a reducing agent and benzoic acid (pKa=4.21) is used as acid (see Examples below).

MODE FOR CARRYING OUT THE INVENTION

<Reductive Alkylation Reaction of Norepinephrine and Acetone>

Prior to the synthesis of [$^{11}$C] isoproterenol, unlabeled isoprotenol was synthesized. 4-(trifluoromethyl) benzoic acid (pKa: 3.69, 1.16 mg 6 µmol) and (R, S)-norepinephrine hydrochloride (6.30 mg 30 µmol) were added to a dried 5 mL eggplant flask, sealed and then replaced with argon. After adding NaBH (OAc)$_3$ (32.8 mg 30 µmol), acetone (0.22 µL 6 µmol) and DMSO/DMF (3:2) (0.4 ml) to make a solution, the solution was heated at 100° C. for 10 minutes. The reaction solution was added with 0.6 mL of 1 N hydrochloric acid to stop the reaction, the solution was diluted with 8.1 mL of CH$_3$CN/ammonium acetate buffer (pH 5.3), added carbazole (82.8 µM DMSO solution, 900 µL, 12.5 µg, 74.5 nmol) as an internal standard substance, and was subjected to (pretreatment) HPLC analysis.

(HPLC Column, Conditions, Etc.)

Figure 1:
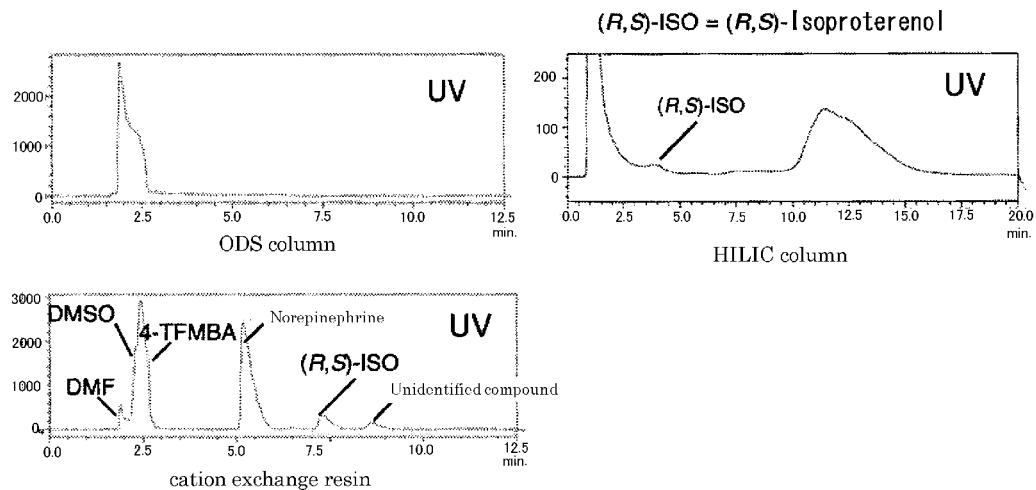
FIG. 1 shows the results of HPLC analysis of DMF and DMSO solution containing commercially available norepinephrine and isoproterenol (non-activated), p-trifluoromethylbenzoic acid (4-TFMBA), and NaBH(OAc)$_3$ by using various columns.

In ODS column and HILIC column, which are generally used in general, it was difficult to isolate the target compound from the reaction mixture (see the upper part of FIG. 1). In contrast, when a cation exchange resin column (sulfonic acid resin column) was used, (R, S)-isoproterenol could be separated with high purity (see the lower part of FIG. 1)

Analysis Conditions when ODS Column was Used:
Column: CAPCELL PAK C 18, 4.6 (i.d.)×150 mm; eluent: CH$_3$CN/20 mM NaH$_2$PO$_4$=1:99 (v/v); flow rate: 1 mL/min; detection: detector: UV, 254 nm Analysis Conditions when HILIC is Used:
Column: Inertsil Amide, 4.6 (i.d.)×150 mm; eluent: CH$_3$CN/20 mM NaH$_2$PO$_4$=80:20 (v/v); flow rate: 2 mL/min; detector: UV, 254 nm Conditions when cation exchange resin column is used: see paragraph 0021

<Synthesis of [2-$^{11}$C] Acetone>

The [$^{11}$C] CO$_2$ produced by the $^{14}$N (p, α) $^{11}$C reaction of the cyclotron was mixed with introduced into a first reactor containing a mixed solution of methyllithium (0.7 mL, about 1 mol/L diethylether solution, 700 µmol) and cyclopentylmethylether (hereinafter referred to as CPME, 0.5 mL) cooled to keep it below −10° C. After heating for 2 minutes at 85° C., it was cooled to −10° C., then diphenylamine (CPME solution, 0.7 mL, 0.95 mmol) was added. It was kept at that temperature for about 2 minutes and heated at 85° C. for about 1 minute to neutralize excess methyllithium. Subsequently, phenol (0.7 mL CPME solution 1 mmol) was added. By bubbling with nitrogen gas while heating the first reaction vessel at 100° C., [2-$^{11}$C] acetone was captured (1.62 GBq) in the second reaction solution containing a mixed solvent (0.4 mL) of DMSO/DMF (3:2) cooled to below −10° C. The time required from the introduction of [$^{11}$C] CO$_2$ into the first reaction vessel to the capture of [2-$^{11}$C] acetone in the second reaction solution was 14 minutes. The decay corrected yield of [2-$^{11}$C] acetone obtained calculated based on [$^{11}$C] CO$_2$ was 54%.

Even when DMF was used as a trapping solvent for [2-$^{11}$C] acetone, the same operation was carried out. [2-$^{11}$C] acetone was prepared in the same manner using tetrahydrofuran solvent of methyllithium, and [2-$^{11}$C] acetone was captured (4.32 GBq) in a second reaction vessel containing DMF (Required time 17 minutes, decay corrected yield 63%).

[2-$^{11}$C] acetone was confirmed by co-injection with unlabeled acetone on HPLC (mobile phase, CH$_3$CN and 20 mM sodium dihydrogen phosphate (pH 4.8)=1:99, CAPCELL PAK C 18, 4.6 (id)×150 mm; flow rate, 1 mL/min; UV detection, 254 nm; retention time, 4.5 min).

[Formula 4]

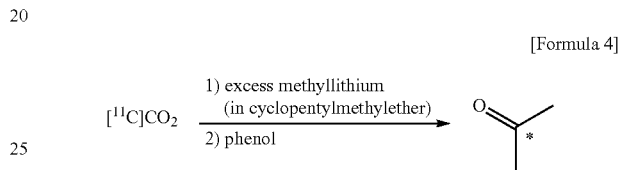

Figure 2:
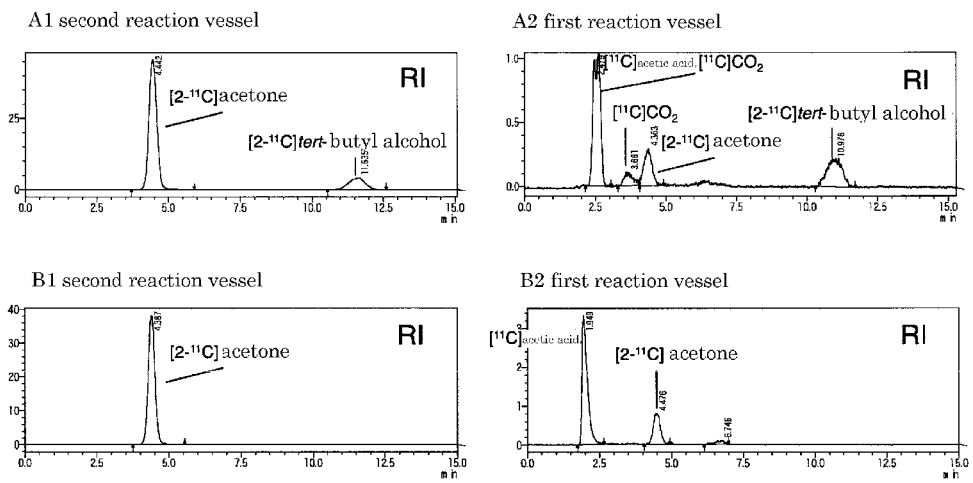
FIG. 2 are (A1) a radio HPLC analysis chart of the labeled compound captured in the second reaction vessel by heating and nitrogen bubbling after preparation of [2-$^{11}$C] acetone, and (A2) a radio HPLC analysis chart of the residue of the first reaction vessel when diphenylamine THF solution/ hydrogen chloride diethyl ether solvent was used as a quenching agent. Also, FIG. 2 are (B1) a radio HPLC analysis chart of the labeled compound captured in the second reaction vessel by heating and nitrogen bubbling after preparation of [2-$^{11}$C] acetone, and (B2) a radio HPLC analysis chart of the residue of the first reaction vessel when a diphenylamine THF solution/phenol THF solution is used as a quenching agent.

The production efficiency of [2-$^{11}$C] acetone was investigated when using a combination of a THF solution of diphenylamine and a diethyl ether solution of hydrogen chloride as a quenching agent after preparation of acetone. After the reaction in the first reaction solution, the labeled compound captured in the second reaction solution containing a mixed solution of DMSO and DMF cooled to 0° C. or less was analyzed, and it was found that acetone and [2-$^{11}$C] tert-butyl alcohol (See A1 in FIG. 2). In addition, a large amount of diethylether solvent, which interferes with the reductive alkylation reaction, was transferred to the second reaction vessel together with [2-$^{11}$C] acetone. Neutralization of excess methyllithium with diphenylamine is insufficient, and [2-$^{11}$C] tert-butyl alcohol is by-produced from [2-11C] acetone produced in the process of neutralization with strong acid. From the results of actual HPLC analysis, no iminium ion or aldol condensate between [2-$^{11}$C] acetone and diphenylamine has been confirmed (see A2 in FIG. 2). In this way, only the target [2-$^{11}$C] acetone could be obtained (see B2 in FIG. 2), and the transfer of the solvent to the second reaction vessel was suppressed.

Reductive Alkylation Reaction of Norepinephrine and [2-$^{11}$C] Acetone

Example 1

A reductive alkylation reaction of [2-$^{11}$C] acetone synthesized as described above with norepinephrine was carried out to synthesize [$^{11}$C] isoproterenol.

[Formula 5]

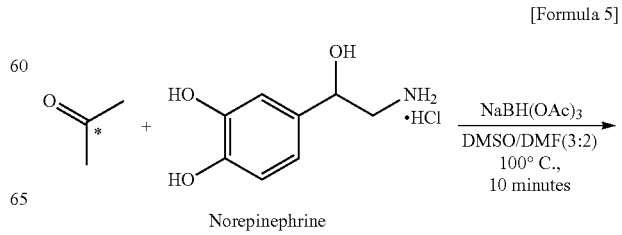

Norepinephrine

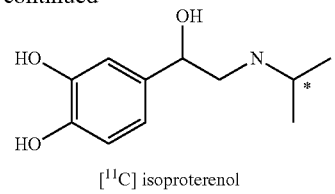

[11C] isoproterenol

The mixture with sodium triacetoxyborohydride (NaBH (OAc)) (32.6 mg, 149 μmol), 4-(trifluoromethyl) benzoic acid (pKa: 3.69, 1.20 mg, 6 μmol) mg 30 μmol), DL-norepinephrine hydrochloride (6.36 (6.36 mmol)), and 0.4 ml of DMSO/DMF (3:2) was cooled and kept below −10° C. until the introduction of [2-11C] acetone was complete. [2-11C] acetone was gasified by heating at 100° C. and transferred to a reaction vessel containing the above mixture by a nitrogen gas stream. After heating at 100° C. for 10 minutes in a closed system, it was diluted with ammonium acetate buffer solution (pH 5.3, 1.6 mL) and purified by preparative HPLC (mobile phase, CH$_3$CN/acetic acid-ammonium acetate buffer (pH 5.2) 10:90; column, CAPCELL PAK SCX UG 80, 20 (id)×250 mm; flow rate, 10 mL/min; UV detection, 278 nm; retention time, 25 min).

Figure 3:
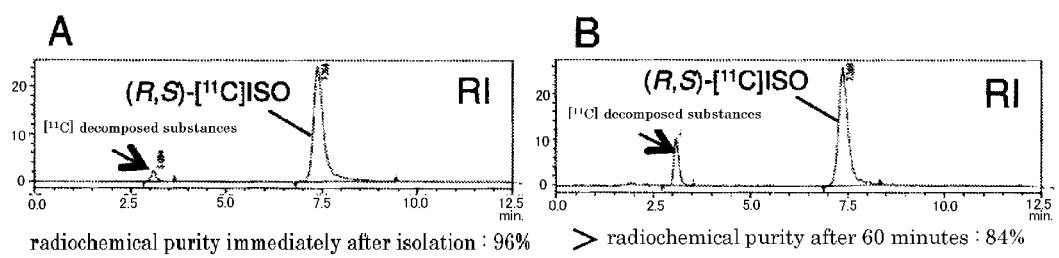
FIG. 3 is a chart showing the results of HPLC analysis of the synthesized [$^{11}$C] isoproterenol solution (without addition of tartaric acid) immediately after isolation (A) and 60 minutes after isolation (B).
Figure 4:
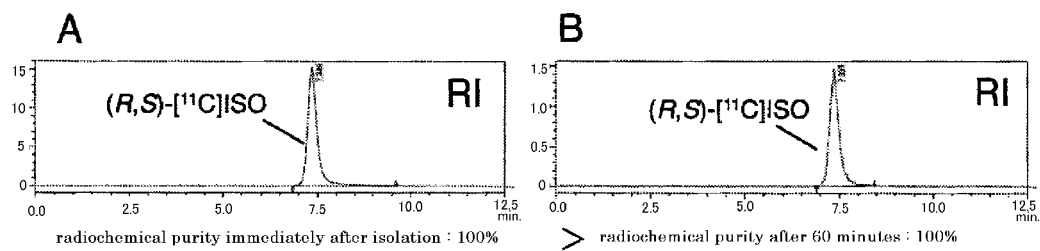
FIG. 4 is a chart showing the results of HPLC analysis of the synthesized [$^{11}$C] isoproterenol solution (with tartaric acid addition) immediately after isolation (A) and after 60 minutes from isolation (B).

Radiochemical purity and chemical purity of [2-11C] isoproterenol in the solution after HPLC fractionation were analyzed by HPLC (CH$_3$CN/acetic acid-ammonium acetate (pH 5.3), 10:90; column, CAPCELL PAK SCX UG 80, 4.6 (id)×150 mm; flow rate, 1 mL/min; UV detection, 278 nm; retention time, 6.5 min). [11C] isoproterenol was confirmed by co-injection of unlabeled isoproterenol in HPLC. In the absence of addition of tartaric acid, the radiochemical purity immediately after isolation was 96%, whereas the radiochemical purity after 60 minutes dropped to 84% (see FIG. 3). In contrast, when tartaric acid was added, no drop in radiochemical purity was observed even after 60 minutes (see FIG. 4). This is presumed to be due to inhibition of deprotonation of two adjacent phenolic hydroxyl groups present in the catechol nucleus under acidic conditions and suppression of subsequent oxidative decomposition by oxygen molecules or superoxide. Also, the chemical purity measured at the above wavelength was >93%

EXAMPLES 2 TO 10

In Examples 2 to 10, [11C] isoproterenol was synthesized by performing a reductive alkylation reaction of norepinephrine with [2-11C]acetone under various conditions shown in Table 1.

TABLE 1

| Entry[a] | Reducing agent (equivalent for norepinephrine) | Acid (equivalent for norepinephrine) | Solvent | Yield[b] (%) |
|---|---|---|---|---|
| Example 2 | NaBH$_3$CN (1.3) | — | ethylene glycol | 68[c] |
| Example 3 | NaBH$_3$CN (1.4) | CH$_3$COOH (1) | ethylene glycol | 75 |
| Example 4 | NaBH$_3$CN (1.1) | CH$_3$COOH (2) | ethylene glycol | 79 |
| Example 5 | NaBH$_3$CN (1.2) | Benzoic acid (1) | ethylene glycol | 72 |
| Example 6 | NaBH(OAc)$_3$ (0.12) | CH$_3$COOH (1) | DMSO/DMF (60:40 v/v) | 65 |
| Example 7 | NaBH(OAc)$_3$ (1.3) | CH$_3$COOH (1) | DMSO/DMF (60:40 v/v) | 75 |
| Example 8 | NaBH(OAc)$_3$ (1.1) | Benzoic acid (1) | DMSO/DMF (60:40 v/v) | 86 |
| Example 9 | NaBH(OAc)$_3$ (1.1) | Benzoic acid (2) | DMSO/DMF (60:40 v/v) | 87 |
| Example 10 | NaBH(OAc)$_3$ (1.0) | p-TFMBA (1) | DMSO/DMF (60:40 v/v) | 79 |

[a]Reaction of [2-11C]acetone and (R,S)-norepinephrine (30 μmol) was carried out in the presence of NaBH$_3$CN or NaBH(OAc)$_3$ in solvent (400 μL) under the heating by setting at 100° C. for 10 min.
[b]HPLC analytical yield of [11C]isoproterenol was calculated by peak area ratio of the [11C]compounds distributions. The identification of [11C]isoproterenol was conducted by co-injecting with the corresponding non-radioactive isoproterenol.
[c]When (R,S)-norepinephrine hydrochloride salt was used as a substrate without neutralization, the yield was decreased to 57%.

That is, in Example 2, [11C] isoproterenol was synthesized by reacting sodium cyanoborohydride (NaBH$_3$CN) and DL-norepinephrine hydrochloride with ethylene glycol as a solvent without adding acid. In addition, in Example 3 and Example 4, [11C] isoproterenol was synthesized in the same manner except that acetic acid was added as an acid. Furthermore, in Example 5, benzoic acid was used as an acid, and [11C] isoproterenol was similarly synthesized. Further, in Examples 6 and 7, [11C] isoproterenol was synthesized by reacting sodium triacetoxyborohydride (NaBH (OAc)) with DL-norepinephrine hydrochloride by using DMSO/DMF (3:2) as a solvent and acetic acid as an acid. Further, in Examples 8 and 9, [11C] isoproterenol was synthesized by reacting sodium triacetoxyborohydride (NaBH (OAc)) and DL-norepinephrine hydrochloride by using DMSO/DMF (3:2) as a solvent and benzoic acid as an acid. Further, in Example 10, [C]isoproterenol was synthesized by reacting sodium triacetoxyborohydride (NaBH (OAc)) and DL-norepinephrine hydrochloride by using DMSO/DMF (3:2) as a solvent and 4-(Trifluoromethyl) benzoic acid as an acid.

Details of the synthesis procedure and analysis method in Example 3 will be described below as an example. The other examples can be carried out in accordance with the procedure of the Example 3.

DL-norepinephrine hydrochloride (6.36 mg, 30 μmol) was weighed in a dry flask purged with argon and a 25 wt. % methanol solution of tetramethylammonium hydroxide (12.6 μL, 30 μmol) was added under ice cooling, and the solution was concentrated under reduced pressure and dried. A mixed solution was prepared by adding sodium cyanoborohydride (2.1 mg, 33 μmol), acetic acid (3.43 μL, 60 μmol), and ethylene glycol (0.4 mL), and the mixture was cooled to −10° C. until introduction of [2-11C] acetone was completed. [2-11C] acetone was gasified by heating at 100° C. and transferred to a reactor containing the above mixture under a nitrogen gas flow. After heating at 100° C. for 10 minutes in a closed system, hydrochloric acid (1 mol/L, 0.1 mL) was added and diluted with ammonium acetate buffer (pH 5.3, 1.5 mL) and analyzed by HPLC (mobile phase, CH$_3$CN/Analysis by acetic acid-ammonium acetate buffer, (pH 5.2) 10:90; column, CAPCELL PAK SCX UG 80, 4.6 (id)×250 mm; flow rate 1 mL/min; UV detection, 254 nm; retention time, 13 min).

<Result>

As shown in Table 1, in Examples 2 to 10, the objective [11C]isoproterenol was obtained in a high yield (by radio HPLC analysis) of 65% or more. Also, in the case of using sodium cyanoborohydride (NaBH$_3$CN) as the reducing agent, Example 3 and Example 4 using acetic acid (pKa=4.76) as the acid was higher yield than Example 5 using benzoic acid (pKa=4.21) as the acid. Further, in the case of using sodium triacetoxyborohydride (NaBH (OAc)$_3$ as a reducing agent, Examples 8 and 9 using benzoic acid (pKa=4.21) as the acid was higher yield than Example 6, 7 using acetic acid (pKa=4.76) and Example 10 using 4-(Trifluoromethyl) benzoic acid.

In addition to the scope of claims, the above embodiments have the following technical features (1) to (4).

(1) A method for producing [2-$^{11}$C] acetone by reacting [$^{11}$C] CO$_2$ with methyllithium, wherein an acid (phenol) having a pKa value of 9 or more and 12 or less is used as a reaction terminator.

(2) The method for producing [2-$^{11}$C] acetone according to (1), wherein the reaction terminator is phenol or a phenol derivative.

(3) The method for producing [2-$^{11}$C] acetone according to (1), wherein an ether compound having a boiling point of 80° C. or higher is used as a reaction solvent.

(4) The method for producing a compound having a partial structure of $^{11}$C-labeled isopropylamine including a reductive alkylation reaction of a primary amine compound or a secondary amine compound and [2-$^{11}$C]acetone in the presence of a reducing agent.

In the method for producing [2-$^{11}$C] acetone of the above (3), since an ether compound having a boiling point of 80° C. or higher is used as a reaction solvent, hygroscopicity is lowered and it is possible to reduce the contamination of moisture which inhibits the reaction. In addition, when it is used for a reductive alkylation reaction, contamination of an ether solvent inhibiting a reductive alkylation reaction can be suppressed to a low level. More preferred is an ether solvent (for example, cyclopentyl methyl ether or the like) at 100° C. or higher.

PET probes of various physiologically active compounds having a partial structure of isopropylamine can be synthesized by using the production method of the above (4). For example, it is bisoprolol (ß receptor blocker) which is a secondary amine compound, Disopyramide (sodium channel inhibitor) which is a tertiary amine compound, Roscovitine (cyclin dependent kinase inhibitor), LY-53,857 (5-HT2 antagonist) and the like.

The present invention is not limited to the embodiments and examples of the invention. Various modifications are also included in the present invention as long as those skilled in the art can easily devise without departing from the scope of the claims.

INDUSTRIAL APPLICABILITY

By utilizing the present invention, development of [2-$^{11}$C] isoproterenol into animal and human clinical research becomes possible, and it is expected to obtain useful pharmacokinetic images (especially brain images). In addition, by conducting the PET microdose test using [11C]isoproterenol, relationships between plasma concentration of isoproterenol and brain concentration are clarified, and the lowest effective concentration in the brain that can be achieved without side effects in humans is determined. It also serves as a basis for dose setting in Phase 2 trials as a tau aggregation inhibitor. Furthermore, isoproterenol itself becomes a promising candidate compound for the treatment of dementia drugs, and the use of isoproterenol as a biomarker can also be useful for narrowing down the optimal compounds by early diagnosis of Alzheimer's disease and evaluation of pharmacological efficacy of various drug candidate compounds.

The invention claimed is:

1. A PET probe comprising $^{11}$C-labeled catechol derivative represented by the following general formula (a) (wherein R is a substituent having an isopropylamino group, and the carbon at the 2-position of the isopropylamino group is labeled with $^{11}$C)

[Formula (a)]

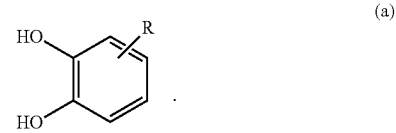

(a)

2. The $^{11}$C-labeled catechol derivative according to claim 1, wherein the $^{11}$C-labeled catechol derivative is represented by the following structural formula (b) (wherein carbon of * is labeled with 11C)

[Formula (b)]

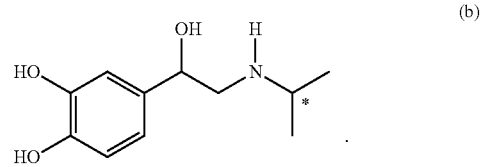

(b)

3. A PET probe comprising the $^{11}$C-labeled catechol derivative according to claim 2.

4. An imaging method of $^{11}$C-labeled catechol, comprising administering the PET probe of claim 3 to a living body, and photographing a PET image.

5. A method for producing the $^{11}$C-labeled catechol derivative according to either claim 1 or claim 2, comprising performing reductive alkylation reaction of catechol derivative represented by the following general formula (c) (wherein R1 represents a substituent having a primary or secondary amine) and [2-$^{11}$C] acetone in the presence of reducing agent

[Formula (c)]

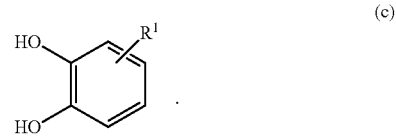

(c)

6. The method for producing the $^{11}$C-labeled catechol derivative according to claim 5, wherein the catechol derivative represented by the general formula (c) is norepinephrine.

7. The method for producing the $^{11}$C-labeled catechol derivative according to claim 6, characterized by using an acid catalyst having a pKa value of 3.7 to 4.8.

* * * * *